(12) United States Patent
Durette et al.

(10) Patent No.: US 6,221,888 B1
(45) Date of Patent: Apr. 24, 2001

(54) SULFONAMIDES AS CELL ADHESION INHIBITORS

(75) Inventors: Philippe L. Durette, New Providence; William K. Hagmann, Westfield; Malcolm Maccoss, Freehold; Sander G. Mills, Scotch Plains; Richard A. Mumford, Red Bank, all of NJ (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 09/424,823

(22) PCT Filed: May 29, 1998

(86) PCT No.: PCT/US98/10952

§ 371 Date: Nov. 29, 1999

§ 102(e) Date: Nov. 29, 1999

(87) PCT Pub. No.: WO98/53818

PCT Pub. Date: Dec. 3, 1998

Related U.S. Application Data

(60) Provisional application No. 60/066,787, filed on Nov. 25, 1997, and provisional application No. 06/047,954, filed on May 29, 1997.

(51) Int. Cl.[7] .................... A61K 31/18; C07C 311/05; C07C 311/06; C07D 213/52; C07D 333/22

(52) U.S. Cl. ............... 514/357; 514/438; 514/604; 546/336; 546/337; 549/76; 549/77; 564/91; 564/97; 564/99

(58) Field of Search ................. 514/604, 357, 514/438; 546/336, 337; 549/76, 77; 564/91, 97, 99

(56) References Cited

U.S. PATENT DOCUMENTS 5,510,332  4/1996  Kogan et al. .
5,663,297 * 9/1997  Alig et al. .
5,780,454 * 7/1998  Adams et al. .
6,083,903 * 7/2000  Adams et al. .

FOREIGN PATENT DOCUMENTS 91 57253    * 6/1997  (JP).
WO 95/12611   5/1995  (WO).
WO 95/15973   6/1995  (WO).
WO 96/01644   1/1996  (WO).
WO 96/06108   2/1996  (WO).
WO 96/20216   7/1996  (WO).
WO 96/22966   8/1996  (WO).
WO 96/31206  10/1996  (WO).
WO 96/35711  11/1996  (WO).
WO 96/40781  12/1996  (WO).
WO 97/02289   1/1997  (WO).
WO 97/03094   1/1997  (WO).
WO 99/06390   2/1999  (WO).
WO 99/06433   2/1999  (WO).
WO 99/06435   2/1999  (WO).

OTHER PUBLICATIONS

Schroff, Hitesh N., et al. Bioorganic & Medicinal Chemistry Letters, vol. 6, No. 21 pp. 2495–2500 (1996).
Jackson, David Y. et al. Med. Chem., 40 pp. 3359–3368 (1997).

* cited by examiner

Primary Examiner—Joseph K. McKane
Assistant Examiner—Taofiq A. Solola
(74) Attorney, Agent, or Firm—Mollie M. Yang; David L. Rose

(57) ABSTRACT

Compounds of Formula I are antagonists of VLA-4 and/or $\alpha_4\beta_7$, and as such are useful in the inhibition or prevention of cell adhesion and cell-adhesion mediated pathologies. These compounds may be formulated into pharmaceutical compositions and are suitable for use in the treatment of asthma, allergies, inflammation, multiple sclerosis, and other inflammatory and autoimmune disorders.

10 Claims, No Drawings

US 6,221,888 B1

SULFONAMIDES AS CELL ADHESION INHIBITORS

This application is a 371 of PCT/US98/10952 filed May 29, 1998, which claims the benefit of 60/066,787, filed Nov. 25, 1997, which claims the benefit of 60/047,954, filed May 29, 1997.

SUMMARY OF THE INVENTION

The compounds of the present invention are antagonists of the VLA-4 integrin ("very late antigen-4"; CD49d/CD29; or $\alpha_4\beta_1$) and/or the $\alpha_4\beta_7$ integrin (LPAM-1 and $\alpha_4\beta p$), thereby blocking the binding of VLA-4 to its various ligands, such as VCAM-1 and regions of fibronectin and/or ($\alpha_4\beta_7$ to its various ligands, such as MadCAM-1, VCAM-1 and fibronectin. Thus, these antagonists are useful in inhibiting cell adhesion processes including cell activation, migration, proliferation and differentiation. These antagonists are useful in the treatment, prevention and suppression of diseases mediated by VLA-4 and/or $\alpha_4\beta_7$ binding and cell adhesion and activation, such as multiple sclerosis, asthma, allergic rhinitis, allergic conjunctivitis, inflammatory lung diseases, rheumatoid arthritis, septic arthritis, type I diabetes, organ transplantation, restenosis, autologous bone marrow transplantation, inflammatory sequelae of viral infections, myocarditis, inflammatory bowel disease including ulcerative colitis and Crohn's disease, certain types of toxic and immune-based nephritis, contact dermal hypersensitivity, psoriasis, tumor metastasis, and atherosclerosis.

BACKGROUND OF THE INVENTION

The present invention relates to sulfonamide derivatives which are useful for the inhibition and prevention of leukocyte adhesion and leukocyte adhesion-mediated pathologies. This invention also relates to compositions containing such compounds and methods of treatment using such compounds.

Many physiological processes require that cells come into close contact with other cells and/or extracellular matrix. Such adhesion events may be required for cell activation, migration, proliferation and differentiation. Cell—cell and cell-matrix interactions are mediated through several families of cell adhesion molecules (CAMs) including the selecting, integrins, cadherins and immunoglobulins. CAMs play an essential role in both normal and pathophysiological processes. Therefore, the targetting of specific and relevant CAMs in certain disease conditions without interfering with normal cellular functions is essential for an effective and safe therapeutic agent that inhibits cell-cell and cell-matrix interactions.

The integrin superfamily is made up of structurally and functionally related glycoproteins consisting of $\alpha$ and $\beta$ heterodimeric, transmembrane receptor molecules found in various combinations on nearly every mammalian cell type. (for reviews see: E. C. Butcher, Cell, 67, 1033 (1991); T. A. Springer, Cell, 76, 301(1994); D. Cox et al., "The Pharmacology of the Integrins." Medicinal Research Rev. 14, 195 (1994) and V. W. Engleman et al., "Cell Adhesion Integrins as Pharmaceutical Targets." in Ann. Repts. in Medicinal Chemistry, Vol. 31, J. A. Bristol, Ed.; Acad. Press, N.Y., 1996, p. 191).

VLA-4 ("very late antigen-4"; CD49d/CD29; or ($\alpha_4\beta_1$) is an integrin expressed on all leukocytes, except platelets and mature neutrophils, including dendritic cells and macrophage-like cells and is a key mediator of the cell—cell and cell-matrix interactions of of these cell types (see M. E. Hemler, "VLA Proteins in the Integrin Family: Structures, Functions, and Their Role on Leukocytes." Ann. Rev. Immunol. 8, 365 (1990)). The ligands for VLA-4 include vascular cell adhesion molecule-1 (VCAM-1) and the CS-1 domain of fibronectin (FN). VCAM-1 is a member of the Ig superfamily and is expressed in vivo on endothelial cells at sites of inflammation. (See R. Lobb et al. "Vascular Cell Adhesion Molecule 1." in Cellular and Molecular Mechanisms of Inflammation, C. G. Cochrane and M. A. Gimbrone, Eds.; Acad. Press, San Diego, 1993, p. 151.) VCAM-1 is produced by vascular endothelial cells in response to pro-inflammatory cytokines (See A. J. H. Gearing and W. Newman, "Circulating adhesion molecules in disease.", Immunol. Today, 14, 506 (1993). The CS-1 domain is a 25 amino acid sequence that arises by alternative splicing within a region of fibronectin. (For a review, see R. O. Hynes "Fibronectins.", Springer-Velag, N.Y., 1990.) A role for VLA-V4CS-1 interactions in inflammatory conditions has been proposed (see M. J. Elices, "The integrin $\alpha_4\beta_1$ (VLA-4) as a therapeutic target" in Cell Adhesion and Human Disease, Ciba Found. Symp., John Wiley & Sons, N.Y., 1995, p. 79).

$\alpha_4\beta_7$ (also referred to as LPAM-1 and $\alpha_4\beta p$) is an integrin expressed on leukocytes and is a key mediator of leukocyte trafficking and homing in the gastrointestinal tract (see C. M. Parker et al., Proc. Natl. Acad. Sci. USA, 89, 1924 (1992)). The ligands for $\alpha_4\beta_7$ include mucosal addressing cell adhesion molecule-1 (MadCAM-1) and, upon activation of $\alpha_4\beta_7$, VCAM-1 and fibronectin (Fn). MadCAM-1 is a member of the Ig superfamily and is expressed in vivo on endothelial cells of gut-associated mucosal tissues of the small and large intestine ("Peyer's Patches") and lactating mammary glands. (See M. J. Briskin et al., Nature, 363, 461 (1993); A. Hamann et al., J. Immunol., 152, 3282 (1994)). MadCAM-1 can be induced in vitro by proinflammatory stimuli (See E. E. Sikorski et al. J. Immunol., 151, 5239(1993)). MadCAM-1 is selectively expressed at sites of lymphocyte extravasation and specifically binds to the integrin, $\alpha_4\beta_7$.

Neutralizing anti-$\alpha_4$ antibodies or blocking peptides that inhibit the interaction between VLA-4 and/or $\alpha_4\beta_7$ and their ligands have proven efficacious both prophylactically and therapeutically in several animal models of disease, including i) experimental allergic encephalomyelitis, a model of neuronal demyelination resembling multiple sclerosis (for example, see T. Yednock et al., "Prevention of experimental autoimmune encephalomyelitis by antibodies against $\alpha_4\beta_1$ integrin." Nature, 356, 63 (1993) and E. Keszthelyi et al., "Evidence for a prolonged role of $\alpha_4$ integrin throughout active experimental allergic encephalomyelitis." Neuology, 47, 1053 (1996)); ii) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leucocyte recruitment and bronchial hyperresponsiveness in the guinea-pig." Eur. J. Pharmacol., 282, 243 (1995)); iii) adjuvant-induced arthritis in rats as a model of inflammatory arthritis (see C. Barbadillo et al., "Anti-VLA-4 mAb prevents adjuvant arthritis in Lewis rats." Arthr. Rheuma. (Suppl.), 36 95 (1993) and D. Seiffge, "Protective effects of monoclonal antibody to VLA-4 on leukocyte adhesion and course of disease in adjuvant arthritis in rats." J. Rheumatol., 23, 12 (1996)); iv) adoptive autoimmune diabetes in the NOD mouse (see J. L. Baron et al., "The pathogenesis of adoptive murine autoimmune diabetes requires an interaction between $\alpha_4$-integrins and vascular cell adhesion molecule-1.", J. Clin. Invest., 93, 1700 (1994), A. Jakubowski et al., "Vascular cell adhesion molecule-Ig fusion protein selectively targets activated $\alpha_4$-integrin receptors in vivo: Inhibition of autoimmune diabetes in an adoptive transfer model in nonobese diabetic mice." J. Immunol., 155, 938 (1995), and X. D. Yang et al., "Involvement of beta 7 integrin and mucosal addressin cell adhesion molecule-1 (MadCAM-1) in the development of diabetes in nonobese diabetic mice", Diabetes, 46, 1542 (1997)); v) cardiac allograft survival in mice as a model of organ transplantation (see M. Isobe et al., "Effect of anti-VCAM-1 and anti-VLA-4 monoclonal antibodies on cardiac allograft survival and response to soluble antigens in mice.", *Transplant. Proc.*, 26, 867 (1994) and S. Molossi et al., "Blockade of very late antigen-4 integrin binding to fibronectin with connecting segment-1 peptide reduces accelerated coronary arteripathy in rabbit cardiac allografts." *J. Clin Invest.*, 95, 2601 (1995)); vi) spontaneous chronic colitis in cotton-top tamarins which resembles human ulcerative colitis, a form of inflammatory bowel disease (see D. K. Podolsky et al., "Attenuation of colitis in the Cotton-top tamarin by anti-$\alpha_4$ integrin monoclonal antibody.", *J. Clin. Invest.*, 92, 372 (1993)); vii) contact hypersensitivity models as a model for skin allergic reactions (see T. A. Ferguson and T. S. Kupper, "Antigen-independent processes in antigen-specific immunity.", *J. Immunol.*, 150, 1172 (1993) and P. L. Chisholm et al., "Monoclonal antibodies to the integrin α-4 subunit inhibit the murine contact hypersensitivity response." *Eur. J. Immunol.*, 23, 682 (1993)); viii) acute neurotoxic nephritis (see M. S. Mulligan et al., "Requirements for leukocyte adhesion molecules in nephrotoxic nephvitis.", *J. Clin. Invest.*, 91, 577 (1993)); ix) tumor metastasis (for examples, see M. Edward, "Integrins and other adhesion molecules involved in melanocytic tumor progression.", *Curr. Opin. Oncol.*, 7, 185 (1995)); x) experimental autoimmune thyroiditis (see R. W. McMurray et al., "The role of $\alpha_4$ integrin and intercellular adhesion molecule-1 (ICAM-1) in murine experimental autoimmune thyroiditis." *Autoimmunity*, 23, 9 (1996); and xi) ischemic tissue damage following arterial occlusion in rats (see F. Squadrito et al., "Leukocyte integrin very late antigen-4/vascular cell adhesion molecule-1 adhesion pathway in splanchnic artery occlusion shock." *Eur. J. Pharmacol.*, 318, 153 (1996; xii) inhibition of TH2 T-cell cytokine production including IL-4 and IL-5 by VLA-4 antibodies which would attenuate allergic responses (J.Clinical Investigation 100, 3083 (1997). The primary mechanism of action of such antibodies appears to be the inhibition of lymphocyte and monocyte interactions with CAMs associated with components of the extracellular matrix, thereby limiting leukocyte migration to extravascular sites of injury or inflammation and/or limiting the priming and/or activation of leukocytes.

There is additional evidence supporting a possible role for VLA-4 interactions in other diseases, including rheumatoid arthritis; various melanomas, carcinomas, and sarcomas; inflammatory lung disorders; acute respiratory distress syndrome (ARDS); atherosclerotic plaque formation; restenosis; uveitis and circulatory shock (for examples, see A. A. Postigo et al., "The $\alpha_4\beta_1$/VCAM-1 adhesion pathway in physiology and disease.", *Res. Immunol.*, 144, 723 (1994) and J.-X. Gao and A. C. Issekutz, "Expression of VCAM-1 and VLA-4 dependent T-lymphocyte adhesion to dermal fibroblasts stimulated with proinflammatory cytokines." *Immunol.* 89, 375 (1996)).

At present, there is a humanized monoclonal antibody (Antegren® Athena Neurosciences/Elan ) against VLA-4 in clinical development for the treatment of "flares" associated with multiple sclerosis and a humanized monoclonal antibody (ACT-1®/LDP-02 LeukoSite) against $\alpha_4\beta_7$ in clinical development for the treatment of inflammatory bowel disease. Several peptidyl antagonists of VLA-4 have been described (D. Y. Jackson et al., "Potent $\alpha_4\beta_1$ peptide antagonists as potential anti-inflammatory agents", *J. Med. Chem.*, 40, 3359 (1997); H. N. Shroff et al., "Small peptide inhibitors of $\alpha_4\beta_7$ mediated MadCAM-1 adhesion to lymphocytes", *Bioorg. Med. Chem. Lett.*, 6, 2495 (1996); U.S. Pat. No. 5,510,332, WO97/03094, WO97/02289, WO96/40781, WO96/22966, WO96/20216, WO96/01644, WO96/06108, WO95/15973). There is one report of non-peptidyl inhibitors of the ligands for $\alpha_4$-integrins (WO96/31206). There still remains a need for low molecular weight, specific inhibitors of VLA-4- and $\alpha_4\beta_7$-dependent cell adhesion that have improved pharmacokinetic and pharmacodynamic properties such as oral bioavailability and significant duration of action. Such compounds would prove to be useful for the treatment, prevention or suppression of various pathologies mediated by VLA-4 and $\alpha_4\beta_7$ binding and cell adhesion and activation.

DETAILED DESCRIPTION OF THE INVENTION

One aspect of the present invention provides a method for the treatment of diseases, disorders, conditions or symptoms mediated by cell adhesion in a mammal which comprises administering to said mammal an effective amount of a compound Formula I:

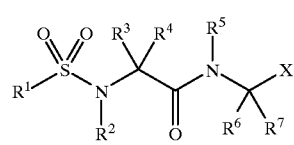

I or a pharmaceutically acceptable salt thereof wherein:
$R^1$ is 1) $C_{1-10}$alkyl,
  2) $C_{2-10}$alkenyl,
  3) $C_{2-10}$alkynyl,
  4) Cy,
  5) Cy-$C_{1-10}$alkyl,
  6) Cy-$C_{2-10}$alkenyl,
  7) Cy-$C_{2-10}$alkynyl,
wherein alkyl, alkenyl, and alkynyl are optionally substituted with one to four substituents independently selected from $R^a$; and Cy is optionally substituted with one to four substituents independently selected from $R^b$;
$R^2$ and $R^3$ are independently selected from
  1) hydrogen, or
  2) a group selected from $R^1$;
$R^4$ is 1) hydrogen,
  2) $C_{1-10}$alkyl,
  3) $C_{2-10}$alkenyl,
  4) $C_{2-10}$alkynyl,
  5) aryl,
  6) aryl-$C_{1-10}$alkyl,
  7) heteroaryl,
  8) heteroaryl-$C_{1-10}$alkyl,
wherein alkyl, alkenyl, and alkynyl are optionally substituted with one to four substituents independently selected from $R^a$; and aryl and heteroaryl optionally substituted with one to four substituents independently selected from $R^b$; or $R^3$, $R^4$ and the carbon to which they are attached form a 3–7 membered mono- or bicyclic ring containing 0–2 heteroatoms selected from N, O and S;
$R^5$ is 1) hydrogen,
  2) $C_{1-10}$alkyl,
  3) Cy, or
  4) Cy-$C_{1-10}$alkyl,
wherein alkyl is optionally substituted with one to four substituents independently selected from $R^a$; and Cy is optionally substituted with one to four substituents independently selected from $R^b$;
$R^6$ is 1) hydrogen,
  2) $C_{1-10}$alkyl,
  3) $C_{2-10}$alkenyl,
  4) $C_{2-10}$alkynyl,
  5) Cy,
  6) Cy-$C_{1-10}$alkyl,
  7) Cy-$C_{2-10}$alkenyl,
  8) Cy-$C_{2-10}$alkynyl,
wherein alkyl, alkenyl and alkynyl are optionally substituted with one to four substituents selected from $R^x$, and Cy is optionally substituted with one to four substituents independently selected from $R^y$;

$R^7$ is 1) hydrogen,
    2) $C_{1-10}$alkyl,
    3) $C_{2-10}$alkenyl,
    4) $C_{2-10}$alkynyl,
    5) aryl,
    6) aryl-$C_{1-10}$allkyl,
    7) heteroaryl,
    8) heteroaryl-$C_{1-10}$alkyl, wherein alkyl, alkenyl and alkynyl are optionally substituted with one to four substituents selected from Rx, and aryl and heteroaryl are optionally substituted with one to four substituents independently selected from $R^y$; or $R^6$, $R^7$ together with the atoms to which they are attached form a 3–7 membered ring containing 0–2 heteroatoms selected from N, O and S;

$R^a$ is 1) Cy, or
    2) a group selected from Rx;
wherein Cy is optionally substituted with one to four substituents independently selected from $R^c$;

$R^b$ is 1) a group selected from $R^a$,
    2) $C_{1-10}$alkyl,
    3) $C_{2-10}$alkenyl,
    4) $C_{2-10}$alkynyl,
    5) $C_{1-10}$alkyl,
    6) heteroaryl $C_{1-10}$alkyl, wherein alkyl, alkenyl, alkynyl, aryl, heteroaryl are optionally substituted with a group independently selected from $R^c$;

$R^c$ is 1) halogen,
    2) amino,
    3) carboxy,
    4) $C_{1-4}$alkyl,
    5) $C_{1-4}$alkoxy,
    6) aryl,
    7) aryl $C_{1-4}$alkyl, or
    8) aryloxy;

$R^d$ and $R^e$ are independently selected from hydrogen, $C_{1-10}$alkyl, $C_{2-10}$alkenyl, $C_{2-10}$alkynyl, Cy and Cy $C_{1-10}$alkyl, wherein alkyl, alkenyl, alkynyl and Cy is optionally substituted with one to four substituents independently selected from $R^c$; or $R^d$ and $R^e$ together with the atoms to which they are attached form a heterocyclic ring of 5 to 7 members containing 0–2 additional heteroatoms independently selected from oxygen, sulfur and nitrogen;

$R^f$ and $R^g$ are independently selected from hydrogen, $C_{1-10}$alkyl, Cy and Cy $C_{1-10}$alkyl; or $R^f$ and $R^g$ together with the carbon to which they are attached form a ring of 5 to 7 members containing 0–2 heteroatoms independently selected from oxygen, sulfur and nitrogen;

$R^h$ is 1) hydrogen,
    2) $C_{1-10}$alkyl,
    3) $C_{2-10}$alkenyl,
    4) $C_{2-10}$alkynyl,
    5) cyano,
    6) aryl,
    7) aryl $C_{1-10}$alkyl,
    8) heteroaryl,
    9) heteroaryl $C_{1-10}$alkyl, or
    10) —$SO_2R^i$;

wherein alkyl, alkenyl, and alkynyl are optionally substituted with one to four substituents independently selected from $R^a$; and aryl and heteroaryl are each optionally substituted with one to four substituents independently selected from $R^b$;

$R^i$ is 1) $C_{1-10}$alkyl
    2) $C_{2-10}$alkenyl,
    3) $C_{2-10}$alkynyl, or
    4) aryl;

wherein alkyl, alkenyl, alkynyl and aryl are each optionally substituted with one to four substituents independently selected from $R^c$;

$R^x$ is 1) —$OR^d$,
    2) —$NO_2$,
    3) halogen
    4) —$S(O)_mR^d$,
    5) —$SR^d$,
    6) —$S(O)_2OR^d$,
    7) —$S(O)_mNR^dR^e$,
    8) —$NR^dR^e$,
    9) —$O(CR^fR^g)_nNR^dR^e$,
    10) —$C(O)R^d$,
    11) —$CO_2R^d$,
    12) —$CO_2(CR^fR^g)_nCONR^dR^e$,
    13) —$OC(O)R^d$,
    14) —CN,
    15) —$C(O)NR^dR^e$,
    16) —$NR^dC(O)R^e$,
    17) —$OC(O)NR^dR^e$,
    18) —$NR^dC(O)OR^e$,
    19) —$NR^dC(O)NR^dR^e$,
    20) —$CR^d(N—OR^e)$, or
    21) —$CF_3$;

$R^y$ is 1) a group selected from $R^x$,
    2) $C_{1-10}$alkyl,
    3) $C_{2-10}$alkenyl,
    4) $C_{2-10}$alkynyl,
    5) aryl $C_{1-10}$alkyl,
    6) heteroaryl $C_{1-10}$alkyl,
    7) cycloalkyl,
    8) heterocyclyl;

wherein alkyl, alkenyl, alkynyl and aryl are each optionally substituted with one to four substituents independently selected from Rx; Cy is cycloalkyl, heterocyclyl, aryl, or heteroaryl;

m is an integer from 1 to 2;
n is an integer from 1 to 10;

X is 1) —$C(O)OR^d$,
    2) —$P(O)_2OR^d$,
    3) —$S(O)_mOR^d$,
    4) —$C(O)NR^dR^h$, or
    5) -5tetrazolyl.

In one embodiment of the present method compounds of formula I are those wherein $R^1$ is Cy. For the purpose of $R^1$ Cy is preferably aryl optionally substituted with one to four substituents selected from $R^b$. More preferred $R^1$ is phenyl with a substituent on the 3-position and optionally a second substituent; the more preferred substituents are selected from $C_{1-10}$alkoxy, halogen, cyano, and trifluoromethyl.

In another embodiment of the present method compounds of Formula I are those wherein $R^2$ is H or $C_{1-6}$alkyl. Preferred $R^2$ is H or $C_{1-3}$alkyl, more preferably H or methyl.

In another embodiment of the present method compounds of Formula I are those wherein one of $R^3$ and $R^4$ is other than hydrogen. In a preferred embodiment one of $R^3$ and $R^4$ is hydrogen and the other is Cy, Cy-$C_{1-10}$alkyl, or $C_{1-10}$alkyl, each of which is optionally substituted as provided under Formula I. For the purpose of $R^3/R^4$ Cy is preferably aryl or heteroaryl each optionally substituted with one to four substituents selected from $R^b$; and alkyl is optionally substituted with one to four substituents independently selected from $R^a$. More preferred $R^3/R^4$ is selected from phenyl; Cy-$C_{1-3}$alkyl wherein Cy is thienyl, pyridyl or phenyl optionally substituted with one or two groups selected from phenyl, hydroxy, halogen, cyano, and nitro; and $C_{1-6}$alkyl optionally substituted with $CO_2H$ or $CONH_2$.

Yet in another embodiment of the present method compounds of Formula I are those wherein one of $R^6$ and $R^7$ is other than hydrogen. In a preferred embodiment one of $R^6$ and $R^7$ is hydrogen and the other is aryl, aryl-$C_{1-10}$alkyl, or $C_{1-10}$alkyl, wherein aryl is optionally substituted with one to four substituents independently selected from $R^y$, and alkyl is optionally substituted with one to four substituents selected from $R^x$. More preferred $R^6/R^7$ is selected from aryl-$C_{1-3}$alkyl wherein aryl is phenyl or naphthyl each optionally substituted with one or two groups selected from $R^y$.

Yet in another embodiment of the present method compounds of Formula I are those wherein X is —C(O)O$R^d$.

In a more preferred embodiment, the cell adhesion is mediated by VLA-4, and the compounds are of Formula Ia as described hereinbelow.

In another aspect the present invention provides compounds of formula Ia:

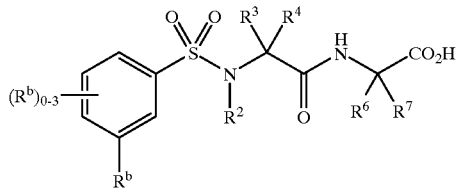

Ia or a pharmaceutically acceptable salt thereof,
wherein
$R^2$ is 1) hydrogen, or
2) $C_{1-6}$alkyl;
one of $R^3$ and $R^4$ is hydrogen and the other is
1) aryl,
2) heteroaryl,
3) aryl-$C_{1-10}$alkyl,
4) heteroaryl-$C_{1-10}$alkyl, or
5) $C_{1-10}$alkyl,
wherein aryl and heteroaryl are each optionally substituted with one to four substituents selected from $R^b$; and alkyl is optionally substituted with one to four substituents independently selected from $R^a$; or $R^3$, $R^4$ and the carbon to which they are attached form a 3–7 membered mono- or bicyclic ring containing 0–2 heteroatoms selected from N, O and S;
one of $R^6$ and $R^7$ is hydrogen and the other is
1) aryl,
2) aryl-$C_{1-10}$alkyl, or
3) $C_{1-10}$alkyl,
wherein aryl is optionally substituted with one to four substituents independently selected from $R^y$, and alkyl is optionally substituted with one to four substituents selected from $R^x$; and $R^a$, $R^b$, $R^x$ and $R^y$ are as defined above under Formula I.

In a more preferred embodiment of compounds of Formula Ia, $R^b$ is selected from $C_{1-10}$alkoxy, halogen, cyano, and trifluoromethyl; $R^2$ is H or methyl; one of $R^3$ and $R^4$ is hydrogen and the other is phenyl, Cy-$C_{1-3}$alkyl (wherein Cy is thienyl, pyridyl or phenyl optionally substituted with one or two groups selected from phenyl, hydroxy, halogen, cyano, and nitro); and $C_{1-6}$alkyl optionally substituted with $CO_2H$ or $CONH_2$; one of $R^6$ and $R^7$ is hydrogen and the other is aryl-$C_{1-2}$alkyl, wherein aryl is optionally substituted with one to two substituents independently selected from halogen; and $R^y$ is as defined above under Formula I.

The present compounds are generally composed of three domains: 1) a sulfonyl moiety, 2) amino acid 1, and 3) amino acid 2, and are named in a manner similar to that used to name oligopeptides. Representative names used herein and their corresponding structures are shown below (without the stereochemistry) to illustrate the nomenclature used in the application. N-(3,4-dimethoxybenzenesulfonyl)(L)-3-(2-thienyl)alanyl-(L)-norleucine

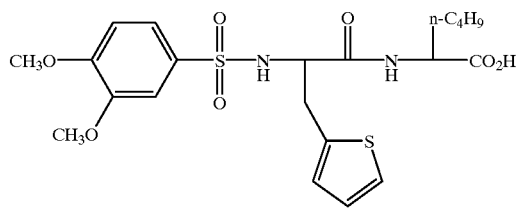

N-(3,5-dichlorobenzenesulfonyl)-(L-N-methylvalyl-(L)-2-naphthylalanine

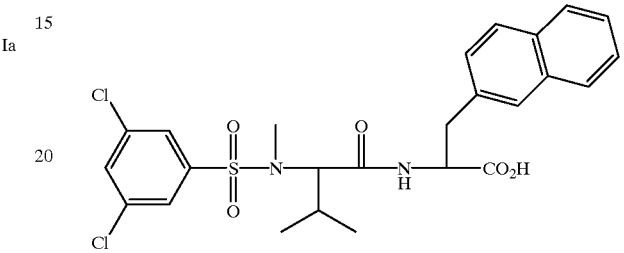

N-(3-chlorobenzenesulfonyl)-2-amino-indan-2-carbonyl-(L)-4-fluorophenylalanine

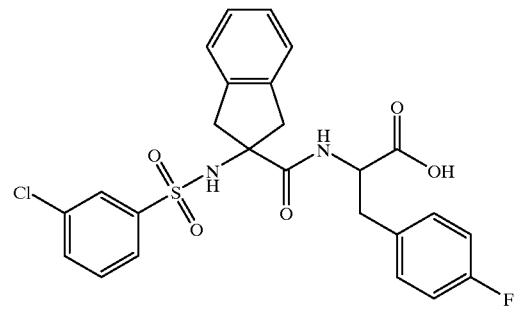

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon—carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon—carbon triple bond, and which may be linear or branched or combinations thereof. Examples of alkyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, benzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuiranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H) pyrimidine-2,4-diones (N-substituted uracils).

"Halogen" includes fluorine, chlorine, bromine and iodine.

Optical Isomers - Diastereomers - Geometric Isomers - Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Formula I to antagonize the actions of VLA-4 and/or $\alpha_4\beta_7$ integrin makes them useful for preventing or reversing the symptoms, disorders or diseases induced by the binding of VLA-4 and or $\alpha_4\beta_7$ to their various respective ligands. Thus, these antagonists will inhibit cell adhesion processes including cell activation, migration, proliferation and differentiation. Accordingly, another aspect of the present invention provides a method for the treatment (including prevention, alleviation, amelioration or suppression) of diseases or disorders or symptoms mediated by VLA-4 and/or $\alpha_4\beta_7$ binding and cell adhesion and activation, which comprises administering to a mammal an effective amount of a compound of Formula I. Such diseases, disorders, conditions or symptoms are for example (1) multiple sclerosis, (2) asthma, (3) allergic rhinitis, (4) allergic conjunctivitis, (5) inflammatory lung diseases, (6) rheumatoid arthritis, (7) septic arthritis, (8) type I diabetes, (9) organ transplantation rejection, (10) restenosis, (11) autologous bone marrow transplantation, (12) inflammatory sequelae of viral infections, (13) myocarditis, (14) inflammatory bowel disease including ulcerative colitis and Crohn's disease, (15) certain types of toxic and immune-based nephritis, (16) contact dermal hypersensitivity, (17) psoriasis, (18) tumor metastasis, and (19) atherosclerosis.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of | 1 mL |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

-continued

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to:

(a) other VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflanmmatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib; h) inhibitors of phosphodiesterase type IV (PDE-IV); (i) antagonists of the chemokine receptors, especially CCR-1, CCR-2, and CCR-3; () cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) antidiabetic agents such as insulin, sulfonylureas, biguanides (metformin), α-glucosidase inhibitors (acarbose) and glitazones (troglitazone, pioglitazone, enghtazone, MCC-555, BRL49653 and the like); (1) preparations of interferon beta (interferon beta-1a, interferon beta-1b); (m) anticholinergic agents such as muscarinic antagonists (ipratropimn bromide); (n) other compounds such as 5-aminosalicylic acid and prodrugs thereof, antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Compounds of the present invention may be prepared by procedures illustrated in the accompanying schemes. In the first method (Scheme 1), a resin-based synthetic strategy is outlined where the resin employed is represented by the ball (●). An N-Fmoc-protected amino acid derivative A (Fmoc=fluorenylmethoxycarbonyl) is loaded on to the appropriate hydroxyl-containing resin using dicyclohexylcarbodiimide (DCC) and 1-hydroxybenzotriazole (HOBt) in dimethylformamide (DMF) to give B. The Fmoc protecting group is removed with piperidine in DMF to yield free amine C. The next Fmoc-protected amino acid derivative D is coupled to C employing standard peptide (in this instance, 2-1H-benzotriazol-1-yl)-1,1,3,3-tetramethyluronium hexafluorophosphate (HBTU), HOBt, and N,N-diisopropylethylamine (DIEA) in DMF) to yield dipeptide E. The Fmoc group is removed with piperidine in DMF to yield the free amine F. A sulfonyl chloride derivative is reacted with F in the presence of DIEA to yield G. The final product is removed from the resin with strong acid (in this instance, trifluoroacetic acid (TFA) in the presence of thioanisole and dithiane) to yield compounds of the present invention H.

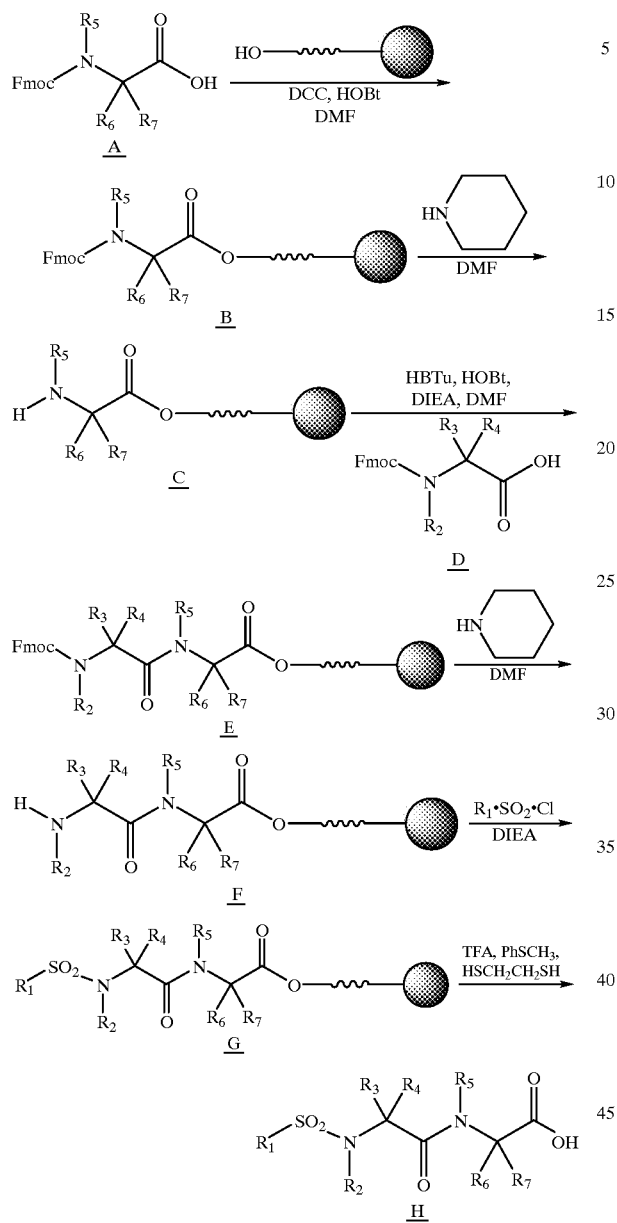

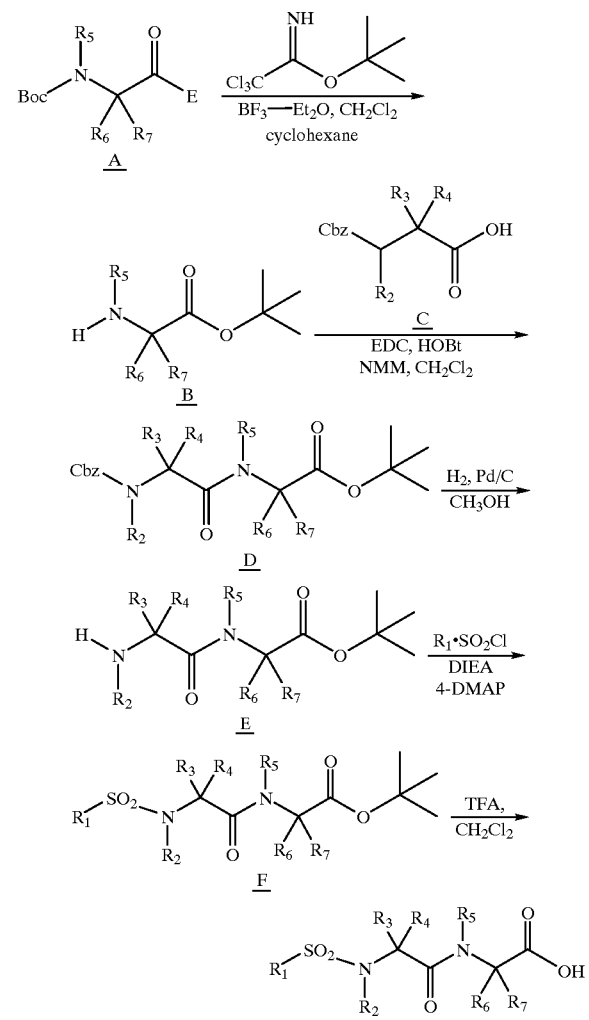

In the second method (Scheme 2), standard solution phase synthetic methodology is outlined. An N-Boc-protected amino acid derivative A (Boc=tert-butyloxycarbonyl) is treated with tert-butyl 2,2,2-trichloroacetimidate in the presence of boron trifluoride etherate to yield tert-butyl ester B which is subsequently coupled to Cbz-protected amino acid derivative C (Cbz=carbobenzyloxy) in the presence of 1-(3-dimethylaminopropyl)-3-ethylcarbodiimide hydrochloride (EDC), HOBt, and N-methylmorpholine (NMM) in methylene chloride (CH$_2$Cl$_2$) to yield dipeptide D. Catalytic hydrogenation of D in the presence of a palladiulm-on-carbon (Pd/C) catalyst yields E. Reaction of E with a sulfonyl chloride in the presence of DIEA and 4-dimethylaminopyridine (DMAP) yields F which is subsequently reacted with strong acid (TFA) to yield the desired product G.

GENERAL PROCEDURES FOR THE SOLID-PHASE SYNTHESIS OF COMPOUNDS OF FORMULA I.

Step A. Loading of N-Fmoc-amino acid derivatives onto resins.

N-Fmoc-amino acids were loaded on either Wang® (Calbiochem-Novabiochem Corp.) or Chloro (2-chlorotrityl) resin. Wang® resin, typically 0.3 mmol, was washed with dimethylformamide three times. A solution of N-Fmoc-amino acid (0.3 mmol) in dimethylformamide (3 mL) was transferred to the pre-swollen Wang® resin. Dicyclohexylcarbodiimide (0.3 -mmol) and 1-N-hydroxybenztriazole (0.3 mmol) was added and the mixture gently swirled for 2 hours. Following filtration, the resin was sequentially washed with dimethylfonnamide (3 times) and dichloromethane (3 times). The amino acid substitution value obtained after vacuum drying typically ranged between 0.07 to 0.1 mmol.

Alternatively, Chloro (2-chorotrityl) resin, typically 0.2 mmol, was pre-swollen in dimethylformamide. A solution of N-Fmoc-amino acid (0.2 mmol) in dimethylformamide (3 ml) was added to the resin, followed by the addition of N,N-diisopropylethylamine(0.4 mmol). The resin was gently stirred for 2 hours, filtered and washed sequentially with dimethylformamide (3 times) and dichloromethane (3 times). The resin was finally washed with 10% methanol in dichloromethane and vacuum dried. The amino acid substitution value obtained after vacuum drying typically ranged between 0.05 to 0.1 mmol.

Step B. Deprotection of the N-Fmoc group.

The N-Fmoc protecting group was removed from the resin from Step A by treatment with 20% pipezidine in dimethylformamide for 30 minutes. Following filtration, the resin was washed sequentially with dimethylformamide (3 times), dichloromethane (1 time) and dimethylformamide (2 times) and used in the subsequent reaction.

Step C. Coupling of the next N-Fmoc-amino acid derivative

A solution of the next desired N-Fmoc-amino acid derivative (0.4 mmol) in dimethylformamide (2 mL) was mixed with 2-(1H-benzotriazol-1-yl)-1,1,3,3-tetramethyluronium hexafluorophosphate (0.4 mmol), 1-N-hydroxybenztriazole (0.4 mmol) and diisopropylethylamine (0.6 mmol). This solution was transferred to resin from Step B and typically allowed to react for 2 hours. Couplings were monitored by ninhydrin reaction. The coupling mixture was filtered and the resin washed with dimethylformamide (3 times) and used in the subsequent reaction.

Step D. Deprotection of the N-Fmoc group.

The N-Fmoc protecting group was removed from the resin from Step C by the procedure described in Step B and used in the subsequent reaction.

Step E. Acylation (or sulfonylation) of the terminal amino group.

The desired N-terminal capping reagent (sulfonylchloride or acylchloride) (0.4 mol) was dissolved in dimethylformamide (2 mL), mixed with N,N-diisopropylethylamine(0.8 mmol) and added to the resin from Step D. After approximately two hours, the resin was sequentially washed with dimethylformamide (3 times) and dichloromethane (3 times).

Step F. Cleavage of the desired products from the resins.

The final desired products were cleaved from the resins from Step E by gently stirring with a solution of trifluoroacetic acid:thioanisole:ethanedithiol (95:2.5:2.5); 3 hours for Wang® resin and 30 minutes for the Chloro (2-chorotrityl) resin. Following filtration, the solvents were removed by evaporation and the residue dissolved in acetonitrile (3 mL). Insoluble material was removed by filtration. The final products were purified by reverse phase chromatography with a linear gradient of buffer A (0.1% trifluoroacetic acid in water) and buffer B (0.1% trifluoroacetic acid in acetonitrile) and isolated by lyophilization. Molecular ions were obtained by electrospray ionization mass spectrometry or matrix-assisted laser desorption ionization time-of-flight mass spectrometry to confirm the structure of each peptide.

The following compounds were prepared by the general procedure described above using the appropriate amino acid derivatives and sulfonyl chloride. These examples are provided to illustrate the present invention and are not to be construed as limiting its scope in any manner.

| Ex. No. | Compound Name | MS* |
|---|---|---|
| (1) | N-(3,4-dimethoxybenzenesulfonyl)-(L)-3-(2-thienyl)alanyl-norleucine; | 485 |
| (2) | N-(3,4-dimethoxybenzenesulfonyl)-(L)-3,3 diphenylalanyl-(L)-norleucine; | 555 |
| (3) | N-(3,4-dimethoxybenzenesulfonyl)-(L)-aspartyl-(L)-norleucine; | 447 |
| (4) | N-(3,4-dimethoxybenzenesulfonyl)-(L)-3-(3-pyridyl)alanyl-(L)-norleucine; | 481 |
| (5) | N-(3,4-dimethoxybenzenesulfonyl)-(L)-alanyl-(L)-norleucine; | 403 |

-continued

| Ex. No. | Compound Name | MS* |
|---|---|---|
| (6) | N-(3,4-dimethoxybenzenesulfonyl)-(L)-homophenylalanyl-(L)-norleucine; | 493 |
| (7) | N-(3,4-dimethoxybenzenesulfonyl)-(L)-valyl-(L)-3-(2-naphthyl)alanine; | 515 |
| (8) | N-(3,4-dimethoxybenzenesulfonyl)-(L)-asparagyl-(L) norleucine; | 446 |
| (9) | N-(3,4-dimethoxybenzenesulfonyl)-(L)-isoleucyl-(L)-3-(2-naphthyl)alanine; | 529 |
| (10) | N-(3,4-dimethoxybenzenesulfonyl)-(L)-3-(4-biphenyl)-alanyl-(L)-norleucine; | 555 |
| (11) | N-(3,5-dichlorobenzenesulfonyl)-(L)-N-methylvalyl-(L)-3-(2-naphthyl)alanine; | 537 |
| (12) | N-(3,5-di(trifluoromethyl)-benezenesulfonyl)-(L)-N-(L)-3-(2-naphthyl)alanine; | 605 |
| (13) | N-(3,5-dichlorobenzenesulfonyl)2(S)-aminobutyryl-(L)-3-(2-naphthyl)alanine; | 509 |
| (14) | N-(3,4-dimethoxybenzenesulfonyl)-(L)-N-methylisoleucyl-(L)-3-(2-naphthyl)alanine; | 543 |
| (15) | N-(3,4-dimethoxybenzenesulfonyl)-(L)-N-methylvalyl-(L)-3-(2-naphthyl)alanine; | 529 |
| (16) | N-(3,4-dimethoxybenzenesulfonyl)-(L)-sarcosinyl-(L)-3-(2-naphthyl)alanine; | 487 |
| (17) | N-(3,4-dimethoxybenzenesulfonyl)-(L)-phenylalanyl-(L)-norleucine; | 479 |
| (18) | N-(3,4-dimethoxybenzenesulfonyl)-(L)-N-methylphenylalanyl-(L)-norleucine; | 492 |
| (19) | N-(3,4-dimethoxybenzenesulfonyl)-(L)-α-phenylglycyl-(L)-norleucine; | 465 |
| (20) | N-(3,4-dimethoxybenzenesulfonyl)-(L)-N-methylalanyl-(L)-norleucine; | 417 |
| (21) | N-3,5-dichlorobenzenesulphonyl)-(L)-tyrosyl-(L)-4-fluorophenylalanine; | 555 |
| (22) | N-(3,5-dichlorobenzenesulphonyl)-(L)-3-(4 fluorophenylalanine; | 540 |
| (23) | N-3,5-dichlorobenzenesulphonyl)-(L)-3-(4-(L)-4-fluorophenylalanine; | 539.1 |
| (24) | N-(3,5-dichlorobenzenesulphonyl)-(L)-4-fluorophenylalanyl-(L)-4-fluorophenylalanine; | 557.1 |
| (25) | N-(3,5-dichlorobenzenesulphonyl)-(L)-3,5-difluorophenylalanyl-(L)-4-fluorophenylalanine; | 575.1 |
| (26) | N-(3,5-dichlorobenzenesulphonyl)-(L)-3-(2-pyridyl)alanyl-(L)-4-fluorophenylalanine; | 540 |
| (27) | N-3,5-dichlorobenzenesulphonyl)-(L)-N-methylaspartyl-(L)-3-(2-naphthyl)alanine; | 543.3 |
| (28) | N-(3-fluorobenzenesulfphonyl)-(L)-N-methylvalyl-(L)-3-(2-naphthyl)alanine; | 487.2 |
| (29) | N-(3,5-dichlorobenzenesulphonyl)-(L)-4 chlorophenylalanyl-(L)-4-fluorophenylalanine; | 575.1 |
| (30) | N-(3,5-dichlorobenzenesulphonyl)-(L)-4 cyanophenylalanyl-(L)-4-fluorophenylalanine; | 564.0 |
| (31) | N-(3,5-dichlorobenzenesulphonyl)-(L)-4 nitrophenylalanyl-(L)-4-fluorophenylalanine; | 584.1 |
| (32) | N-3,5-dichlorobenzenesulphonyl)-(L)-aspartyl-(L)-4-fluorophenylalanine; | 507.0 |
| (33) | N-(3,5-dichlorobenzenesulphonyl)-(L)-3-(3-pyridyl)alanyl-(L)-4-fluorophenylalanine; | 540.2 |
| (34) | N-(3,5-dichlorobenzenesulphonyl)-(L)-N-methylvalyl-(L)-4-fluorophenylalanine; | 604.2 |
| (35) | N-(3,5-dichlorobenzenesulphonyl)-(D)-N-methylvalyl-(L)-3-(2-naphthyl)alanine; | 537.0 |
| (36) | N-(3-chlorobenzenesulphonyl)-2-amino-indan-2-carbonyl-(L)-4-fluorophenylalanine; | 517.2 |
| (37) | N-(3-fluorobenzenesulfphonyl)-(L)-2-phenylglycyl-(L)-4-fluorophenylalanine; | 475.2 |
| (38) | N-(3,5-dichlorobenzenesulphonyl)-(L)-leucyl-(L)-aspartic acid. | 455.1 |

*m/e, $(M)^+$ or $(M + 1)^+$ or $(M + NH_4)^+$.

EXAMPLE 39

Inhibition of VLA-4 Dependent Adhesion to BSA-CS-1 Conjugate

Step 1. Preparation of CS-1 Coated Plates

Untreated 96 well polystyrene flat bottom plates were coated with bovine serum albumin (BSA; 20 μg/ml) for 2 hours at room temperature and washed twice with phosphate buffered saline (PBS). The albumin coating was next derivatized with 10 μg/ml 3-(2-pyridyldithio) propionic acid N-hydroxysuccminide ester (SPDP), a heterobifunctional crosslinker, for 30 minutes at room temperature and washed twice with PBS. The CS-1 peptide (Cys-Leu-His-Gly-Pro-Glu-Ile-Leu-Asp-Val-Pro-Ser-Thr), which was synthesized by conventional solid phase chemistry and purified by reverse phase HPLC, was next added to the derivatized BSA at a concentration of 2.5 μg/ml and allowed to react for 2 hours at room temperature. The plates were washed twice with PBS and stored at 4° C.

Step 2. Preparation of Fluorescently Labeled Jurkat Cells

Jurkat cells, clone E6-1, obtained from the American Type Culture Collection (Rockville, Md.; cat # ATCC TIIB-152) were grown and maintained in RPMI-1640 culture medium containing 10% fetal calf serum (FCS), 50 units/ml penicillin, 50 μg/ml streptomycin and 2 mM glutamine. Fluorescence activated cell sorter analysis with specific monoclonal antibodies confirmed that the cells expressed both the $\alpha_4$ and $\beta 1$ chains of VLA-4. The cells were centrifuged at 400xg for five minutes and washed twice with PBS. The cells were incubated at a concentration of $2 \times 10^6$ cells/ml in PBS containing a 1 μM concentration of a fluorogenic esterase substrate (2', 7'-bis-(2-carboxyethyl)-5- (and -6)-carboxyfluorescein, acetoxymethyl ester; BCECF-AM; Molecular Probes Inc., Eugene, Oreg.; catalog #B-1150) for 30–60 minutes at 37° C. in a 5% $CO_2$/air incubator. The fluorescently labeled Jurkat cells were washed two times in PBS and resuspended in RPMI containing 0.25% BSA at a final concentration of $2.0 \times 10^6$ cells/ml.

Step 3. Assay Procedure

Compounds of this invention were prepared in DMSO at 100x the desired final assay concentration. Final concentrations were selected from a range between 0.001 nM-100 μM. Three μL of diluted compound, or vehicle alone, were premixed with 300 μL of cell suspension in 96-well polystyrene plates with round bottom wells. 100 μL aliquots of the cell/compound mixture were then transferred in duplicate to CS-1 coated wells. The cells were next incubated for 30 minutes at room temperature. The non-adherent cells were removed by two gentle washings with PBS. The remaining adherent cells were quantitated by reading the plates on a Cytofluor II fluorescence plate reader (Perseptive Biosystems Inc., Framingham, Mass.; excitation and emission filter settings were 485 nm and 530 nm, respectively). Control wells containing vehicle alone were used to determine the level of cell adhesion corresponding to 0% inhibition. Control wells coated with BSA and crosslinker (no CS-1 peptide) were used to determine the level of cell adhesion corresponding to 100% inhibition. Cell adhesion to wells coated with BSA and crosslinker was usually less than 5% of that observed to CS-1 coated wells in the presence of vehicle. Percent inhibition was then calculated for each test well and the $IC_{50}$ was determined from a ten point titration using a validated four parameter fit algorithm.

EXAMPLE 40

Antagonism of VLA-4 Dependent Binding to VCAM-Ig Fusion Protein.

1. Preparation of VCAM-Ig

The signal peptide as well as domains 1 and 2 of human VCAM (GenBank Accession no. M30257) were amplified by PCR using the human VCAM cDNA (R & D Systems) as template and the following primer sequences: 3'-PCR primer:5'-AATTATAATTTGATCAACTTAC CTGTCAATTCTTTTACAGCCTGCC-3'; 5'-PCR primer: 5'-ATAGGAATTCCAGCTGCCACCATGCCTGGGAA-GATGGTCG3'.

The 5'-PCR primer contained EcoRI and PvuII restriction sites followed by a Kozak consensus sequence (CCACC) proximal to the initiator methionine ATG. The 3'-PCR primer contained a BclI site and a splice donor sequence. PCR was performed for 30 cycles using the following parameters: 1 min. at 94° C., 2 min. at 55° C., and 2 min. at 72° C. The amplified region encoded the following sequence of human VCAM-1:

MPGKMVVILGASNILWIMFAASQAFKI-ETTPESRYLAQIGDSVSLTC STTJGCESPFFSWRTQID-SPLNGKVTNEGTTSTLTMNPVSFGNEHSYLC TATCESRKLEKGIQVEIYSFPKDPEIHLSGPLEAGKPI-TVKCSVADVY PFDRLEIDLLKGDILMKSQE-FLEDADRKSLETKSLEVTIFPVIEDIGKV LVCRAKL-HIDEMDSVPTVRQAVXEL. The resulting PCR product of 650 bp was digested with EcoRI and BclI and ligated to expression vector pIg-Tail (R & D Systems, Minneapolis, Minn.) digested with EcoRI and BamHI. The pIg-Tail vector contains the genomic fragment which encodes the hinge region, CH2 and CH3 of human IgG1 (GenBank Accession no. Z17370). The DNA sequence of the resulting VCAM fragment was verified using Sequenase (US Biochemical, Cleveland, Ohio). The fragment encoding the entire VCAM-Ig fusion was subsequently excised from pIg-Tail with EcoRI and NotI and ligated to pCI-neo (Promega, Madison, Wis.) digested with EcoRI and NotI. The resulting vector, designated pCI-neo/VCAM-Ig was transfected into CHO-KL (ATCC CCL 61) cells using calcium-phosphate DNA precipitation (Specialty Media, Lavalette, N.J.). Stable VCAM-Ig producing clones were selected according to standard protocols using 0.2–0.8 mg/ml active G418 (Gibco, Grand Island, N.Y.), expanded, and cell supernatants were screened for their ability to mediate Jurkat adhesion to wells previously coated with 1.5 μg/ml (total protein) goat anti-human IgG (Sigma, St. Louis, Mo.). A positive CHO-K1IVCAM-Ig clone was subsequently adapted to CHO-SFM serum-free media (Gibco) and maintained under selection for stable expression of VCAM-Ig. VCAM-Ig was purified from crude culture supernatants by affinity chromatography on Protein AIG Sepharose (Pierce, Rockford, Ill.) according to the manufacturer's instructions and desalted into 50 mM sodium phosphate buffer, pH 7.6, by ultrafiltration on a YM-30 membrane (Amicon, Beverly, Mass.).

Step 2. Preparation of $^{125}$I-VCAM-Ig

VCAM-Ig was labeled to a specific radioactivity greater that 1000 Ci/mmole with $^{125}$I-Bolton Hunter reagent (New England Nuclear, Boston, Mass.; cat # NEX120-0142) according to the manufacturer's instructions. The labeled protein was separated from unincorporated isotope by means of a calibrated HPLC gel filtration column (G2000SW; 7.5x600 mm; Tosoh, Japan) using uv and radiometric detection.

Step 3. VCAM-Ig Binding Assay

Compounds of this invention were prepared in DMSO at 100x the desired final assay concentration. Final concentrations were selected from a range between 0.001 nM-100 μM. Jurkat cells were centrifuged at 400xg for five minutes and resuspended in binding buffer (25 mM HEPES, 150 mM NaCl, 3 mM KCl, 2 mM glucose, 0.1% bovine serum albumin, pH 7.4). The cells were centrifuged again and resuspended in binding buffer supplemented with $MnCl_2$ at a final concentration of 1 mM. Compounds were assayed in Millipore MHVB multiscreen plates (cat# MHVBN4550, Millipore Corp., Mass.) by making the following additions to duplicate wells: (i) 200 μL of binding buffer containing 1 mM $MnCl_2$; (ii) 20 μL of $^{125}$I-VCAM-Ig in binding buffer containing 1 mM $MnCl_2$ (final assay concentration ~100 μM); (iii) 2.5 μL of compound solution or DMSO; (iv) and $0.5 \times 10^6$ cells in a volume of 30 μL. The plates were incubated at room temperature for 30 minutes, filtered on a vacuum box, and washed on the same apparatus by the addition of 100 μL of binding buffer containing 1 mM $MnCl_2$. After insertion of the multiscreen plates into adapter plates (Packard, Meriden, Conn., cat# 6005178), 100 μL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Control wells in which cells were omitted were used to determine the level of binding corresponding to 100% inhibition. Binding of $^{125}$I-VCAM-Ig in the absence of cells was usually less than 5% of that observed using cells in the presence of vehicle. Percent inhibition was then calculated for each test well and the IC$_{50}$ was determined from a ten point titration using a validated four parameter fit algorithm.

EXAMPLE 41

Antagonism of $\alpha_4\beta_7$ Dependent Binding to VCAM-Ig Fusion Protein.

Step 1. $\alpha_4\beta_7$ Cell line.

RPMI-8866 cells (a human B cell line $\alpha_4^+\beta_1^-\beta_7^+$; a gift from Prof. John Wilkins, University of Manitoba, Canada) were grown in RPMI/10% fetal calf serum/ 100 U penicillin/ 100 μg streptomycin/2 mM Lglutamine at 37° C., 5% carbon dioxide. The cells were pelleted at 1000 rpm for 5 minutes and then washed twice and resuspended in binding buffer (25 mM Hepes, 150 mM NaCl, 0.1% BSA, 3 mM KCl, 2 mM Glucose, pH 7.4).

Step 2. VCAM-Ig Binding Assay

Compounds of this invention were prepared in DMSO at 100x the desired final assay concentration. Final concentrations were selected from a range between 0.001 nM–100 μM. Compounds were assayed in Millipore MHVB multiscreen plates (Cat# MHVBN4550) by making the following sequential additions to duplicate wells: (i) 100 μl/well of binding buffer containing 1.5 mM MnCl$_2$; (ii) 10 μl/well $^{125}$I-VCAM-Ig in binding buffer (final assay concentration <500 μM); (iii) 1.5 μl/well test compound or DMSO alone; (iv) 38 μl/well RPMI-8866 cell suspension (1.25×10$^6$ cells/ well). The plates were incubated at room temperature for 45 minutes on a plate shaker at 200 rpm, filtered on a vacuum box, and washed on the same apparatus by the addition of 100 μL of binding buffer containing 1 mM MnCl$_2$. After insertion of the multiscreen plates into adapter plates (Packard, Meriden, Conn., cat# 6005178), 100 μL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Wells in which cells were omitted were used to determine the level of binding corresponding to 100% inhibition. Percent inhibition was then calculated for each test well and the IC$_{50}$ was determined from a ten point titration using a validated four parameter fit algorithm.

What is claimed is:

1. A compound having the formula Ia:

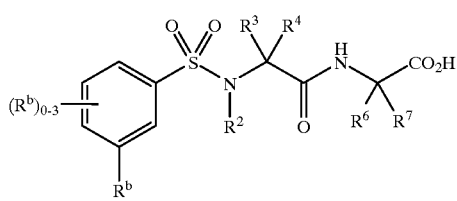

or a pharmaceutically acceptable salt thereof, wherein
$R^2$ is 1) hydrogen, or
2) $C_{1-6}$alkyl;
one of $R^3$ and $R^4$ is hydrogen and the other is
1) aryl,
2) heteroaryl,
3) aryl-$C_{1-10}$alkyl,
4) heteroaryl-$C_{1-10}$alkyl, or
5) $C_{1-10}$alkyl,
wherein aryl and heteroaryl are each optionally substituted with one to four substituents selected from $R^b$; and alkyl is optionally substituted with one to four substituents independently selected from $R^a$; or
$R^3$, $R^4$ and the carbon to which they are attached form a 3–7 membered mono- or bicyclic ring containing 0–2 heteroatoms selected from N, O and S; one of $R^6$ and $R^7$ is hydrogen and the other is
1) aryl,
2) aryl-$C_{1-10}$alkyl, or
3) $C_{1-10}$alkyl,
wherein aryl is optionally substituted with one to four substituents independently selected from $R^y$, and alkyl is optionally substituted with one to four substituents selected from $R^x$; and
$R^a$ is 1) Cy, or
2) a group selected from $R^x$;
wherein Cy is optionally substituted with one to four substituents independently selected from $R^c$;
$R^b$ is 1) a group selected from $R^a$,
2) $C_{1-0}$alkyl,
3) $C_{2-10}$alkenyl,
4) $C_{2-10}$alkynyl,
5) aryl $C_{1-10}$alkyl,
6) heteroaryl $C_{1-10}$alkyl,
wherein alkyl, alkenyl, alkynyl, aryl, heteroaryl are optionally substituted with a group independently selected from $R^c$;
$R^c$ is 1) halogen,
2) amino,
3) carboxy,
4) $C_{1-4}$alkyl,
5) $C_{1-4}$alkoxy,
6) aryl,
7) aryl $C_{1-4}$alkyl, or
8) aryloxy;
$R^d$ and $R^e$ are independently selected from hydrogen, $C_{1-10}$ alkyl, $C_{2-10}$alkenyl, $C_{2-10}$alkynyl, Cy and Cy $C_{1-10}$alkyl, wherein alkyl, alkenyl, alkynyl and Cy is optionally substituted with one to four substituents independently selected from $R^c$; or $R^d$ and $R^e$ together with the atoms to which they are attached form a heterocyclic ring of 5 to 7 members containing 0–2 additional heteroatoms independently selected from oxygen, sulfur and nitrogen;
$R^f$ and $R^g$ are independently selected from hydrogen, $C_{1-10}$alkyl, Cy and Cy $C_{1-10}$alkyl; or $R^f$ and $R^g$ together with the carbon to which they are attached form a ring of 5 to 7 members containing 0–2 heteroatoms independently selected from oxygen, sulfur and nitrogen;
$R^x$ is 1) —OR$^d$,
2) —NO$_2$,
3) halogen
4) —S(O)$_m$R$^d$,
5) —SR$^d$,
6) —S(O)$_2$OR$^d$,
7) —S(O)$_m$NR$^d$R$^e$,
8) —NR$^d$R$^e$,
9) —O(CR$^f$R$^g$)$_n$NR$^d$R$^e$,
10) —C(O)R$^d$, 11) —CO₂R$^d$,
12) —CO₂(CR$^f$R$^g$)$_n$CONR$^d$R$^e$,
13) —OC(O)R$^d$,
14) —CN,
15) —C(O)NR$^d$R$^e$,
16) —NR$^d$C(O)R$^e$,
17) —OC(O)NR$^d$R$^e$,
18) —NR$^d$C(O)OR$^e$,
19) —NR$^d$C(O)NR$^d$R$^e$,
20) —CR$^d$(N—OR$^e$), or
21) —CF₃;

R$^y$ is 1) a group selected from R$^x$,
2) C$_{1-10}$alkyl,
3) C$_{2-10}$alkenyl,
4) C$_{2-10}$alkynyl,
5) aryl C$_{1-10}$alkyl,
6) heteroaryl C$_{1-10}$alkyl,
7) cycloalkyl,
8) heterocyclyl;

wherein alkyl, alkenyl, alkynyl and aryl are each optionally substituted with one to four substituents independently selected from R$^x$;

Cy is cycloalkyl, heterocyclyl, aryl, or heteroaryl;

m is an integer from 1 to 2; and n is an integer from 1 to 10.

2. A compound of claim 1 wherein R$^b$ is selected from C$_{1-10}$alkoxy, halogen, cyano, and trifluoromethyl; R$^2$ is H or methyl; one of R$^3$ and R$^4$ is hydrogen and the other is phenyl, Cy-C$_{1-3}$alkyl (wherein Cy is thienyl, pyridyl or phenyl optionally substituted with one or two groups selected from phenyl, hydroxy, halogen, cyano, and nitro); or C$_{1-6}$alkyl optionally substituted with CO₂H or CONH₂; one of R$^6$ and R$^7$ is hydrogen and the other is aryl-C$_{1-2}$alkyl, wherein aryl is optionally substituted with one to two substituents independently selected from halogen; and R$^y$ is as defined in claim 1.

3. A compound selected from the group consisting of:
N-(3,4dimethoxybenzenesulfonyl)-(L)-3-(2-thienyl)alanyl-norleucine; N-(3,4-dimethoxybenzenesulfonyl)-(L)-3,3-diphenylalanyl-(L)-norleucine; N-3,4-dimethoxybenzenesulfonyl)-(L)-aspartyl-(L)-norleucine; N-(3,4-dimethoxybenzenesulfonyl)(L)-3-(3-pyridyl)alanyl-(L)-norleucine; N-(3,4-dimethoxybenzenesulfonyl)-(L)-alanyl-(L)-norleucine; N-(3,4-dimethoxybenzenesulfonyl)-(L)-homophenylalanyl-(L)-norleucine; N-(3,4-dimethoxybenzenesulfonyl)-L)-valyl-(L)-3-(2-naphthyl)alanine; N-(3,4-dimethoxybenzenesulfonyl)-(L)-asparagyl-(L)-norleucine; N-(3,4-dimethoxybenzenesulfonyl)-(L)-isoleucyl-(L)-3-(2-naphthyl)alanine; N-(3,4-dimethoxybenzenesulfonyl)-(L)-3-(4biphenyl)alanyl-(L)-norleucine; N-(3,5-dichlorobenzenesulfonyl)(L-N-methylvalyl-(L)-3-(2-naphthyl)alanine; N-(3,5-di(trifluoromethyl)-benzenesulfonyl)-(L)-N-methylvalyl-(L)-3-(2-naphthyl)alanine; N-(3,5-dichlorobenzenesulfonyl)-2(S)-aminobutyryl-(L-3-(2-naphthyl)alanine; N-(3,4-dimethoxybenzenesulfonyl)-(L)-N-methylisoleucyl-(L)-3-(2-naphthyl)alanine; N-(3,4-dimethoxybenzenesulfonyl)-(L)-N-methylvalyl-(L)-3-(2-naphthyl)alanine; N-(3,4-dimethoxybenzenesulfonyl)-(L)-sarcosinyl-(L)-3-(2-naphthyl)alanine; N-(3,4-dimethoxybenzenesulfonyl)-(L)-phenylalanyl-(L)norleucine; N-(3,4-dimethoxybenzenesulfonyl)-(L)-N-methylphenylalanyl-(L)-norleucine; N-(3,4-dimethoxybenzenesulfonyl)-(L)-a-phenylglycyl-(L)-norleucine; N-(3,4-dimethoxybenzenesulfonyl)-(L)-N-methylalanyl-(L)-norleucine; N-(3,5-dichlorobenzenesulfonyl)-(L)-tyrosyl-(L)-4-fluorophenylalanine; N-(3,5-dichlorobenzenesulfonyl)-(L-3-(4-pyridyl)alanine4L)-4-fluorophenylalanine; N-(3,5-dichlorobenzenesulfonyl)(L)-phenylalanyl-(L)4-fluorophenylalanine; N-(3,5-ichlorobenzenesulfonyl5(L)4-fluorophenylalanyl-(L)-4-fluorophenylalanine; N-(3,5dichlorobenzenesulfonyl)-(L-3,5fluorophenylalanyl-(L)4-fluorophenylalanine; N-(3,5-dichlorobenzenesulfonyl)-(L-N-methylaspartyl-(L)-2-naphthylalanine; N-(3,5-dichlorobenzenesulfonyl)(L)-3-(2pyridyl)alanyl-(L)4-fluorophenylalanine; N-(3,5-dichlorobenzenesulfonyl)-(L)-N-methylvalyl-(L)-3-(2-naphthyl)alanine; N-(3-fluorobenzenesulfonyl)(L-N-methylvalyl-(L)-3-(2-naphthyl)alanine; N-(3,5-dichlorobenzenesulfonyl)-(L-4-chlorophenylalanyl-(L)-4-fluorophenylalanine; N-(3,5-dichlorobenzenesulfonyl)-(L)4-cyanophenylalanyl-(L)-4-fluorophenylalanine; N-(3,5-dichlorobenzenesulfonyl)(L)-4-nitrophenylalanyl-(L)-4-fluorophenylalanine; N-(3,5-dichlorobenzenesulfonyl)-(L)aspartyl-(L)-4-fluorophenylalanine; N-(3,5-dichlorobenzenesulfonyl)-L)-3(3-pyridyl)alanyl-(L)-4-fluorophenylalanine; and N-(3,5-dichlorobenzenesulfonyl)-(D)-N-methylvalyl-(L)-4-fluorophenylalanine; N-(3,5-dichlorobenzenesulfonyl)4L)-N-methylvalyl-(L)- 3-(2-naphthyl)alanine; N-(3-chlorobenzenesulfonyl)-2-amino-indan-2-carbonyl-(L-4-fluorophenylalanine; N43-fluorobenzenesulfonyl)(L)-2-phenylglycyl-(L)-4-fluorophenylalanine; and N43,5-dichlorobenzenesulfonyl)(L)-leucyl4L)-aspartic acid.

4. A pharmaceutical composition which comprises a compound of claim 1 and a pharmaceutically acceptable carrier thereof.

5. A method for the treatment of diseases or disorders mediated by cell adhesion in a mammal which comprises administering to said mammal an effective amount of a compound of Formula I:

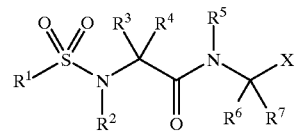

I or a pharmaceutically acceptable salt thereof wherein:
R$^1$ is 1) C$_{1-10}$alkyl,
2) C$_{2-10}$alkenyl,
3) C$_{2-10}$alkynyl,
4) Cy,
5) Cy-C$_{1-10}$alkyl,
6) Cy-C$_{2-10}$alkenyl,
7) Cy-C$_{2-10}$alkynyl,
wherein alkyl, alkenyl, and alkynyl are optionally substituted with one to four substituents independently selected from R$^a$; and Cy is optionally substituted with one to four substituents independently selected from R$^b$;

R$^2$ and R$^3$ are independently selected from
1) hydrogen, or
2) a group selected from R$^1$;
R$_4$ is 1) hydrogen,
2) C$_{1-10}$alkyl,
3) C$_{2-10}$alkenyl,
4) C$_{2-10}$alkynyl,
5) aryl,
6) aryl-C$_{1-10}$alkyl,
7) heteroaryl,
8) heteroaryl-C$_{1-10}$alkyl,
wherein alkyl, alkenyl, and alkynyl are optionally substituted with one to four substituents independently selected from $R^a$; and aryl and heteroaryl optionally substituted with one to four substituents independently selected from $R^b$; or $R^3$, $R^4$ and the carbon to which they are attached form a 3–7 membered mono- or bicyclic ring containing 0–2 heteroatoms selected from N, O and S;

$R^5$ is 1) hydrogen,
2) $C_{1-10}$alkyl,
3) Cy, or
4) Cy-$C_{1-10}$alkyl, wherein alkyl is optionally substituted with one to four substituents independently selected from $R^a$; and Cy is optionally substituted with one to four substituents independently selected from $R^b$;

$R^6$ is 1) hydrogen,
2) $C_{1-10}$alkyl,
3) $C_{2-10}$alkenyl,
4) $C_{2-10}$alkynyl,
5) Cy,
6) Cy-$C_{1-10}$alkyl,
7) Cy-$C_{2-10}$alkenyl,
8) Cy-$C_{2-10}$alkynyl, wherein alkyl, alkenyl and alkynyl are optionally substituted with one to four substituents selected from $R^x$, and Cy is optionally substituted with one to four substituents independently selected from $R^y$;

$R^7$ is 1) hydrogen,
2) $C_{1-10}$alkyl,
3) $C_{2-10}$alkenyl,
4) $C_{2-10}$alkynyl,
5) aryl,
6) aryl-$C_{1-10}$alkyl,
7) heteroaryl,
8) heteroaryl-$C_{1-10}$alkyl, wherein alkyl, alkenyl and alkynyl are optionally substituted with one to four substituents selected from Rx, and aryl and heteroaryl are optionally substituted with one to four substituents independently selected from $R^y$; or $R^6$, $R^7$ together with the atoms to which they are attached form a 3–7 membered ring containing 0–2 heteroatoms selected from N, O and S;

$R^a$ is 1) Cy, or
2) a group selected from Rx;

wherein Cy is optionally substituted with one to four substituents independently selected from $R^c$;

$R^b$ is 1) a group selected from $R^a$,
2) $C_{1-10}$alkyl,
3) $C_{2-10}$alkenyl,
4) $C_{2-10}$alkynyl,
5) aryl $C_{1-10}$alkyl,
6) heteroaryl $C_{1-10}$alkyl, wherein alkyl, alkenyl, alkynyl, aryl, heteroaryl are optionally substituted with a group independently selected from $R^c$;

$R^c$ is 1) halogen,
2) amino,
3) carboxy,
4) $C_{1-4}$alkyl,
5) $C_{1-4}$alkoxy,
6) aryl,
7) aryl $C_{1-4}$alkyl, or
8) aryloxy;

$R^d$ and $R^e$ are independently selected from hydrogen, $C_{1-10}$alkyl, $C_{2-10}$alkenyl, $C_{2-10}$alkynyl, Cy and Cy $C_{1-10}$alkyl, wherein alkyl, alkenyl, alkynyl and Cy is optionally substituted with one to four substituents independently selected from $R^c$; or $R^d$ and $R^e$ together with the atoms to which they are attached form a heterocyclic ring of 5 to 7 members containing 0–2 additional heteroatoms independently selected from oxygen, sulfur and nitrogen;

$R^f$ and $R^g$ are independently selected from hydrogen, $C_{1-10}$alkyl, Cy and Cy $C_{1-10}$alkyl; or $R^f$ and $R^g$ together with the carbon to which they are attached form a ring of 5 to 7 members containing 0–2 heteroatoms independently selected from oxygen, sulfur and nitrogen;

$R^h$ is 1) hydrogen,
2) $C_{1-10}$alkyl,
3) $C_{2-10}$alkenyl,
4) $C_{2-10}$alkynyl,
5) cyano,
6) aryl,
7) aryl $C_{1-10}$alkyl,
8) heteroaryl,
9) heteroaryl $C_{1-10}$alkyl, or
10) —$SO_2R^i$;

wherein alkyl, alkenyl, and alkynyl are optionally substituted with one to four substituents independently selected from $R^a$; and aryl and heteroaryl are each optionally substituted with one to four substituents independently selected from $R^b$;

$R^i$ is 1) $C_{1-10}$alkyl,
2) $C_{2-10}$alkenyl,
3) $C_{2-10}$alkynyl, or
4) aryl;

wherein alkyl, alkenyl, alkynyl and aryl are each optionally substituted with one to four substituents independently selected from $R^c$;

$R^x$ is 1) —$OR^d$,
2) —$NO_2$,
3) halogen
4) —$S(O)_mR^d$,
5) —$SR^d$,
6) —$S(O)_2OR^d$,
7) —$S(O)_mNR^dR^e$,
8) —$NR^dR^e$,
9) —$O(CR^fR^g)_nNR^dR^e$,
10) —$C(O)R^d$,
11) —$CO_2R^d$,
12) —$CO_2(CR^fR^g)_nCONR^dR^e$,
13) —$OC(O)R^d$,
14) —CN,
15) —$C(O)NR^dR^e$,
16) —$NR^dC(O)R^e$,
17) —$OC(O)NR^dR^e$,
18) —$NR^dC(O)OR^e$,
19) —$NR^dC(O)NR^dR^e$,
20) —$CR^d(N—OR^e)$, or
21) —$CF_3$;

$R^y$ is 1) a group selected from $R^x$,
2) $C_{1-10}$alkyl,
3) $C_{2-10}$ alkenyl, 4) $C_{2-10}$ alkynyl,
5) aryl $C_{1-10}$alkyl,
6) heteroaryl $C_{1-10}$alkyl,
7) cycloalkyl,
8) heterocyclyl;

wherein alkyl, alkenyl, alkynyl and aryl are each optionally substituted with one to four substituents independently selected from $R^x$; Cy is cycloalkyl, heterocyclyl, aryl, or heteroaryl;

m is an integer from 1 to 2;

n is an integer from 1 to 10;

X is 1) —C(O)$OR^d$,
2) —P(O)$_2$$OR^d$,
3) —S(O)$_m$$OR^d$,
4) —C(O)$NR^dR^h$, or
5) -5-tetrazolyl.

6. A method of claim 5 wherein said disease is selected from asthma, allergic rhinitis, multiple sclerosis, inflammation, inflammatory bowel disease and atherosclerosis.

7. A method of claim 5 wherein said cell adhesion is mediated by VLA-4(very later antigen-4).

8. A method for the treatment of diseases or disorders, mediated by cell adhesion in a mammal which comprises administering to said mammal an effective amount of a compound of claim 1.

9. A method for the treatment of asthma, allergic rhinitis, multiple sclerosis, atherosclerosis inflammatory bowel disorder, or inflammation in a mammal which comprises administering to said mammal an effective amount of a compound of claim 1.

10. A method of claim 5 wherein in compounds of Formula I $R^1$ is aryl optionally substituted with one to four substituents selected from $R^b$;

$R^2$ is H or $C_{1-3}$alkyl;

$R^3$ is Cy, Cy-$C_{1-10}$alkyl, or $C_{1-10}$alkyl, wherein alkyl is optionally substituted with one to four substituents independently selected from $R^a$; and Cy is optionally substituted with one to four substituents independently selected from $R^b$;

$R^4$ is hydrogen; one of $R^6$ and $R^7$ is hydrogen and the other is aryl, aryl-$C_{1-10}$alkyl, or $C_{1-10}$alkyl, wherein aryl is optionally substituted with one to four substituents independently selected from $R^y$, and alkyl is optionally substituted with one to four substituents selected from $R^x$ X is —C(O)$OR^d$;

$R^b$, $R^d$, $R^x$ and $R^y$ are as defined in claim 5.

* * * * *